United States Patent
Terada et al.

(10) Patent No.: US 9,649,288 B2
(45) Date of Patent: May 16, 2017

(54) INHIBITOR OF VISCERAL FAT LOSS IN PARKINSON'S DISEASE PATIENTS

(75) Inventors: Shin Terada, Yokosuka (JP); Sayuri Yamamoto, Yokosuka (JP)

(73) Assignee: THE NISSHIN OILLIO GROUP, LTD., Tokyo (JP)

( * ) Notice: Subject to any disclaimer, the term of this patent is extended or adjusted under 35 U.S.C. 154(b) by 719 days.

(21) Appl. No.: 13/416,219

(22) Filed: Mar. 9, 2012

(65) Prior Publication Data

US 2012/0171324 A1 Jul. 5, 2012

Related U.S. Application Data

(63) Continuation of application No. PCT/JP2010/066597, filed on Sep. 24, 2010.

(30) Foreign Application Priority Data

Sep. 30, 2009 (JP) ................................. 2009-227191
Oct. 26, 2009 (JP) ................................. 2009-245713

(51) Int. Cl.
| A61K 38/08 | (2006.01) |
| A61K 31/23 | (2006.01) |
| A23L 33/00 | (2016.01) |
| A23L 33/115 | (2016.01) |

(52) U.S. Cl.
CPC ............ *A61K 31/23* (2013.01); *A23L 33/115* (2016.08); *A23L 33/40* (2016.08); *A23V 2002/00* (2013.01)

(58) Field of Classification Search
None
See application file for complete search history.

(56) References Cited

U.S. PATENT DOCUMENTS

| 6,130,244 A * | 10/2000 | DeMichele et al. ........... 514/474 |
| 6,835,750 B1 * | 12/2004 | Henderson .................... 514/557 |
| 2010/0204498 A1 | 8/2010 | Iinuma et al. |

FOREIGN PATENT DOCUMENTS

| WO | WO 2004/022049 | 3/2004 |
| WO | WO 2009/038110 A1 | 3/2009 |

OTHER PUBLICATIONS

Specialty Lipids and Their Biofunctionality by Vigen K. Babayan , May 1985, Harvard Medical School, pp. 417-420.*
How Fat Cells Work by Craig Freudenrich, Ph.D., http://science.howstuffworks.com/life/cellular-microscopic/fat-cell.htm, (c) 2008, pp. 1-4.*
Medium-chain triglyceride (MCT) ketogenic therapy by Yeou-mei Christiana Liu, Wiley Periodicals, Inc. (c) 2008 International League Against Epilepsy, pp. 33-36.*
Lorefalt B., et al., Weight Loss, Body Fat Mass, and Leptin in Parkinson's Disease, Movement Disorders, Apr. 30, 2009, vol. 24, No. 6, p. 885-890.
Matsuo T., et al., Effects of Structured Medium- and Long-Chain Triacylglycerols in Diets with Various Levels of Fat on Body Fat Accumulation in Rats, British Journal of Nutrition, Feb. 2004, vol. 91, No. 2, p. 219-225.
Shinohara H., et al., Randomly Interesterified Triacylglycerol Containing Medium- and Long-Chain Fatty Acids Stimulates Fatty Acid Metabolism in White Adipose Tissue of Rats, Bioscience, Biotechnology, and Biochemistry, Dec. 2006, vol. 70, No. 12, p. 2919-2926.
International Search Report for PCT Application No. PCT/JP2010/066597, mailed Dec. 21, 2010.
Bach A C et al: "The usefulness of dietary medium-chain triglycerides in body weight control: fact or fancy?", Journal of Lipid Research, American Society for Biochemistry and Molecular Biology, Inc, US, vol. 37, No. 4, Jan. 1, 1996 (Jan. 1, 1996), pp. 708-726, XP002975355, ISSN: 0022-2275.
Extended European Search Report for European Patent Application No. 10820459.5, mailed Sep. 16, 2014.

* cited by examiner

*Primary Examiner* — Tamra L Dicus
(74) *Attorney, Agent, or Firm* — Pearl Cohen Zedek Latzer Baratz LLP

(57) ABSTRACT

An inhibitor of visceral fat loss is capable of suppressing body weight loss peculiarly found in Parkinson's disease patients. The inhibitor of visceral fat loss in Parkinson's disease patients of the present invention contains a lipid obtained by subjecting a medium-chain triglyceride that includes as a constitutive fatty acid at least one of a saturated fatty acid having 8 carbon atoms and a saturated fatty acid having 10 carbon atoms to a transesterification reaction with a vegetable oil. The lipid is preferably obtained by subjecting the medium-chain triglyceride to a transesterification reaction with the vegetable oil at a ratio of 10:90 to 20:80.

2 Claims, No Drawings

INHIBITOR OF VISCERAL FAT LOSS IN PARKINSON'S DISEASE PATIENTS

CROSS-REFERENCE TO RELATED APPLICATIONS

This application is a continuation of PCT International Patent Application No. PCT/JP2010/066597, filed Sep. 24, 2010, which is hereby incorporated by reference.

TECHNICAL FIELD

The present invention relates to an inhibitor of visceral fat loss targeted to Parkinson's disease patients.

BACKGROUND ART

Parkinson's disease is a progressive disease that results from disrupted balance of intracerebral neurotransmitters, and causes symptoms such as tremor, bradykinesia and postural reflex disturbance, finally leading to severe physical disorder. In addition, with respect to patients suffering from Parkinson's disease, tendency of occurrence of emaciation has been problematic, which results from body weight loss, as compared with healthy individuals of the same age. Thus far, causes of the body weight loss in Parkinson's disease patients have not been elucidated; however, it has been recently revealed that the body weight loss significantly results from a reduction in the amount of body fat (see Lorefalt B et al., Mov. Disord., 24, pp. 885-890 (2009)).

SUMMARY OF THE INVENTION

Problems to be Solved by the Invention

An object of the present invention is to provide an inhibitor of visceral fat loss, which is capable of suppressing body weight loss peculiarly found in Parkinson's disease patients.

Means for Solving the Problems

The present inventors thoroughly investigated with focus on visceral fat that is one element of body fat, and consequently found that a fat and oil (hereinafter, may be also referred to as "lipid") having a visceral fat loss effect on healthy individuals, i.e., a lipid obtained by subjecting a medium-chain triglyceride to a transesterification reaction with a vegetable oil has an effect of inhibiting a reduction in the amount of visceral fat in Parkinson's disease model rats. Thus, the present invention was completed. Specifically, provided by the present invention are as in the following.

A first aspect of the present invention provides an inhibitor of visceral fat loss in Parkinson's disease patients, the inhibitor including a lipid obtained by subjecting a medium-chain triglyceride that includes as a constitutive fatty acid at least one of a saturated fatty acid having 8 carbon atoms and a saturated fatty acid having 10 carbon atoms to a transesterification reaction with a vegetable oil.

In a second aspect of the inhibitor of visceral fat loss in Parkinson's disease patients according to the first aspect of the present invention, the lipid is obtained by subjecting the medium-chain triglyceride to a transesterification reaction with the vegetable oil at a ratio of 10:90 to 20:80.

A third aspect of the present invention provides use of a lipid for producing a food for inhibiting visceral fat loss in Parkinson's disease patients, the lipid being obtained by subjecting a medium-chain triglyceride that includes as a constitutive fatty acid at least one of a saturated fatty acid having 8 carbon atoms and a saturated fatty acid having 10 carbon atoms to a transesterification reaction with a vegetable oil.

In a forth aspect of the use according to the third aspect of the present invention, the lipid is obtained by subjecting the medium-chain triglyceride to a transesterification reaction with the vegetable oil at a ratio of 10:90 to 20:80.

A fifth aspect of the present invention provides a method for inhibiting visceral fat loss, the method including administering to a Parkinson's disease patient an effective amount of a lipid obtained by subjecting a medium-chain triglyceride that includes as a constitutive fatty acid at least one of a saturated fatty acid having 8 carbon atoms and a saturated fatty acid having 10 carbon atoms to a transesterification reaction with a vegetable oil.

In a sixth aspect of the method for inhibiting visceral fat loss according to the fifth aspect, the lipid is obtained by subjecting the medium-chain triglyceride to a transesterification reaction with the vegetable oil at a ratio of 10:90 to 20:80.

Effects of the Invention

According to the inhibitor of visceral fat loss of the present invention, visceral fat loss in Parkinson's disease patients can be inhibited. Accordingly, suppression of body weight loss peculiarly found in Parkinson's disease patients is enabled.

PREFERRED MODE FOR CARRYING OUT THE INVENTION

Hereinafter, specific embodiments of the present invention are explained in detail; however the present invention is not in any way limited to the following embodiments, and the present invention may be practiced with appropriate modification within the scope of objects thereof.

The inhibitor of visceral fat loss of the present invention is to be administered to a Parkinson's disease patient, and is characterized by including a fat and oil (lipid) obtained by subjecting a medium-chain triglyceride that includes as a constitutive fatty acid at least one of a saturated fatty acid having 8 carbon atoms and a saturated fatty acid having 10 carbon atoms to a transesterification reaction with a vegetable oil. Such a lipid is also referred to as Medium and Long Chain Triglycerides (hereinafter, referred to as MLCT). There is a tendency of occurrence of emaciation due to body weight loss in patients suffering from Parkinson's disease, as compared with healthy individuals of the same age. According to the inhibitor of visceral fat loss of the present invention, administration of the inhibitor to a Parkinson's disease patient enables inhibition of loss of visceral fat that is one element of body fat, and the loss of visceral fat has been considered as a main cause of such body weight loss. The present invention is of significance in that MLCT, which is known to have an effect of visceral fat loss on healthy individuals (PCT International Publication No. 2004/022049), was first found by the inventors hereof to exhibit an effect of inhibiting visceral fat loss on Parkinson's disease patients.

The medium-chain triglyceride that includes as a constitutive fatty acid at least one of a saturated fatty acid having 8 carbon atoms and a saturated fatty acid having 10 carbon atoms is a lipid also referred to as MCT. In the present invention, MCT being a commercially available product or a reagent may be used; however, MCT produced by subjecting a medium-chain fatty acid to an esterification reaction with glycerin according to a common procedure may be also used. The medium-chain fatty acid used as a basic ingredient may be obtained by hydrolyzing, for example, palm kernel oil or coconut oil containing the medium-chain fatty acid, followed by purification. Preferable examples of MCT include those containing as a constitutive fatty acid 75% by mass of a saturated fatty acid having 8 carbon atoms, and 25% by mass of a saturated fatty acid having 10 carbon atoms, and a commercially available product of such MCT is exemplified by an edible lipid manufactured by Nisshin OilliO Group, Ltd. (trade name: ODO).

The vegetable oil preferably has a liquid form at 20° C., and specific examples include soybean oil, rapeseed oil, corn oil, sesame oil, sesame salad oil, Japanese basil oil, linseed oil, peanut oil, safflower oil, sunflower oil, cotton seed oil, grape seed oil, macadamia nut oil, hazelnut oil, pumpkin seed oil, walnut oil, camellia oil, tea seed oil, perilla oil, borage seed oil, olive oil, rice bran oil, wheat germ oil, and the like. These may be used either alone, or two or more thereof may be also used. Of these, rapeseed oil is preferably used.

In an exemplary process for the transesterification reaction of MCT with a vegetable oil, an alkaline catalyst such as sodium methoxide, or an enzyme such as lipase is added as a catalyst to a mixed oil prepared by mixing MCT and a vegetable oil preferably at a ratio of 10:90 to 20:80, and more preferably at a ratio of 10:90 to 15:85, thereby permitting the reaction. It is to be noted that the transesterification reaction is not particularly limited, which may be either a site specific transesterification reaction, or a random transesterification reaction.

For example, in the case in which a random transesterification reaction is allowed using an enzyme, nonspecific lipase or the like may be used as the enzyme. Source of the nonspecific lipase may be any of animals, plants, and microorganisms. Also, the nonspecific lipase may be used directly in the form of powder, or after immobilization. In order to further improve the reaction efficiency, powdery lipase in which no less than 90% of the powder particles have a particle size of 1 to 100 μm is most preferred. The amount of the enzyme used in the random transesterification reaction is preferably 0.01 to 20% by mass, and more preferably 0.1 to 5% by mass with respect to the total mass of the reaction materials. The reaction temperature of the random transesterification reaction is, in light of the durability of the enzyme, preferably 20 to 100° C., and more preferably 40 to 80° C.

In addition, when a random transesterification reaction is carried out using a chemical catalyst, an alkaline chemical catalyst such as sodium methylate or an acidic chemical catalyst such as sulfuric acid may be used. The amount of the chemicals catalyst used in the random transesterification reaction is preferably 0.01 to 5% by mass, and more preferably 0.1 to 2% by mass with respect to the total mass of the reaction materials. The reaction time of the random transesterification reaction is preferably 0.5 to 20 hrs, and more preferably 2 to 5 hrs.

MLCT may be produced by the method explained above, or may be a commercially available product produced by the method explained above. Such a commercially available product is exemplified by an edible lipid manufactured by Nisshin OilliO Group, Ltd. (trade name: HEALTHY RESETTA, a lipid obtained by subjecting MCT to a transesterification reaction with rapeseed oil at a ratio of 14:86).

To the inhibitor of visceral fat loss of the present invention may be added an emulsifying agent for further improving the storage stability. Specific examples of the emulsifying agent include synthetic emulsifying agents such as polyglycerin fatty acid esters, sucrose fatty acid esters, sorbitan fatty acid esters, polysorbates, condensed ricinoleic fatty acid esters and monoglycerin fatty acid esters, and nonsynthetic emulsifying agents such as soybean lecithin, yolk lecithin, soybean lysolecithin, yolk lysolecithin, enzyme treated yolk, saponin, plant sterols and milk fat globule membrane.

The inhibitor of visceral fat loss of the present invention is preferably administered via an oral route. Formulations suited for oral administration include, for example, capsules, tablets, pills, powdered formulations, subtle granules, granules, liquid formulations, syrups, and the like. It is preferred that a formulation in the form of a medical drug composition be prepared containing the lipid added as an active ingredient, and a pharmacologically and pharmaceutically acceptable additive. The pharmacologically and pharmaceutically acceptable additive which may be used includes a substance commonly employed in the field of formulation and does not react with the lipid of the present invention, and examples of the additive include an excipient such as glucose, lactose, crystalline cellulose and starch, as well as a disintegrant, a binding agent, a coating agent, a coloring matter, a diluent, and the like.

The inhibitor of visceral fat loss of the present invention is preferably administered in an amount equivalent to 25 to 45% of the total amount of energy in terms of the sum of the inhibitor of visceral fat loss plus food consumed by a Parkinson's disease patient per day.

Also, the lipid obtained by subjecting a medium-chain triglyceride that includes as a constitutive fatty acid at least one of a saturated fatty acid having 8 carbon atoms and a saturated fatty acid having 10 carbon atoms to a transesterification reaction with a vegetable oil may be used for producing a food for inhibiting visceral fat loss in Parkinson's disease patient. For example, by processing the lipid to pack into a soft capsule, a nutritional supplementary food may be prepared. In addition, processing of the lipid to give powdery oil, liquid emulsified oil or the like enables it to be directly consumed. Alternatively, processing of the same to be utilized in common food enables it to be indirectly consumed.

Common food that can be produced using the lipid is not particularly limit, and examples thereof include bread and confectioneries such as breads, cakes, cookies, biscuits, donuts, muffins, scones, chocolates, snacks, whipped creams and ice creams, beverages such as fruit juice drinks, nutrition drinks and sports drinks, seasoning processed food such as soups, dressings, sauces, mayonnaise, butter, margarine and prepared margarine, fat spread, shortening, bakery mix, cooking oil, frying oil, fried food, processed meat products, frozen food, fried food, noodles, retort food, liquid diet, diet for dysphagia patients, and the like.

The food preferably contains the lipid in an amount equivalent to 25 to 45% of the total amount of energy in terms of the entire food consumed per day, taking into consideration the status of high-fat diet consumed by a Parkinson's disease patient who is suffering from "emaciation".

EXAMPLES

Hereinafter, Examples are shown in order to explain the present invention in more detail, but the present invention is not limited thereto.

Test Example 1

In the present experiment, a Parkinson's disease model rat was used to verify an effect of inhibiting visceral fat loss. It is to be noted that as a lipid source in the feed, a typical vegetable oil (rapeseed oil) was blended, assuming a regular diet in human. Also, as a source for supplying medium-chain fatty acids, MCT or MLCT was blended.

(1) Experimental Animals

Sprague-Dawley male rats were used as experimental animals. 6-Hydroxydopamine was administered to brain striatum of 8-weeks old rats (Japan SLC, Inc.), and the rat in which a symptom of Parkinson's disease (rotational movement resulting from apomorphine stimulation) had been ascertained was used as a Parkinson's disease model rat. Also, a solvent of 0.2% ascorbic acid alone was administered to 8-weeks old rats (Japan SLC, Inc.), which were used as control rats.

(2) Test Feed

Although healthy individuals consume lipid in an amount equivalent to 20 to 25% of the total amount of energy consumed per day, Parkinson's disease patients consume a high lipid diet in an amount equivalent to about 35% of the total amount of energy consumed per day. Taking into consideration this status, the test feed was designed as a high lipid feed to give a formulation such that 39% of the total amount of energy was derived from lipids, thereby providing a level equivalent to the high lipid diet. More specifically, according to the formulation shown in Table 1, each of the powered components other than a lipid (MLCT, rapeseed oil, and MCT) were mixed first, followed by finally mixing the lipid and homogenizing the mixture to prepare a MLCT diet, a vegetable oil diet, and a MCT diet, respectively. It is to be noted that 1% by mass of rapeseed oil was blended in the MCT diet for supplying essential fatty acids.

TABLE 1

| Component (% by mass) | MLCT diet | vegetable oil diet | MCT diet |
| --- | --- | --- | --- |
| corn starch | 26.7486 | 26.7486 | 25.4486 |
| milk casein | 20 | 20 | 20 |
| pregelatinized corn starch | 13.2 | 13.2 | 13.2 |
| granulated sugar | 10 | 10 | 10 |
| MLCT (*1) | 20 | 0 | 0 |
| rapeseed oil (*2) | 0 | 20 | 1 |
| MCT (*3) | 0 | 0 | 20.3 |
| cellulose powder | 5 | 5 | 5 |
| mineral mix | 3.5 | 3.5 | 3.5 |
| vitamin mix | 1 | 1 | 1 |
| L-cystine | 0.3 | 0.3 | 0.3 |
| choline bitartrate | 0.25 | 0.25 | 0.25 |
| tert-butylhydroquinone | 0.0014 | 0.0014 | 0.0014 |

(*1) MLCT (lipid obtained by subjecting MCT to a transesterification reaction with rapeseed oil at a ratio of 14:86): Nisshin OilliO Group, Ltd., trade name "HEALTHY RESETTA"
(*2) rapeseed oil: Nisshin OilliO Group, Ltd., trade name "Nisshin Canola"
(*3) MCT (medium-chain triglyceride): Nisshin OilliO Group, Ltd., trade name "ODO"

(3) Rearing Method

The test was performed with 4 groups in total including three groups (five animals per group) of Parkinson's disease model rats: that consumed the MLCT diet "MLCT diet fed group (Example 1)"; that consumed the vegetable oil diet "Vegetable oil diet fed group (Comparative Example 1)"; and that consumed the MCT diet "MCT diet fed group (Comparative Example 2)", and one group (six animals) of control rats that consumed the vegetable oil diet "control group (Control Example 1)". The grouping was carried out such that the average body weight of the rats in each group before starting the test was similar.

The rats were first reared for taming for one week from 13 weeks old, and thereafter reared for 6 weeks while giving the test feed (Table 1) from 14 weeks old. During the rearing, the rats were separately kept in a stainless mesh cage under conditions of: a temperature of 23±1° C.; humidity of 50±10%; and light-dark cycle switched every 12 hrs (lighted from 8:00 to 20:00), while permitting free consumption of water and the test feed.

(4) Measurement of Amount of Increased Body Weight

The body weight of each rat at a start time of administration of the test feed, and the body weight at autopsy of the rat were measured. Thus, the amount of increased body weight was determined from the difference between each of the respective measurements.

(5) Measurement of Level of Visceral Fat

After the rats completed the 6 week rearing, they were fasted from 9:00 am and were sacrificed from 1:00 μm by bleeding under diethyl ether anesthesia. Epididymis fat, perirenal fat, and mesenterium fat were extirpated, and thereafter each weight was measured to determine the level of epididymal, perirenal, and mesenterium fats. Further, total level of fats of the isolated organs was determined as a level of visceral fat.

(6) Statistical Processing

In the statistical processing, mean and standard deviation were calculated on measurements of each group, and a one way layout dispersion analysis was employed for a significance test. In the test, a significant difference was determined to be present with a significance level of less than 5%.

TABLE 2

|  | Control Example 1 | Example 1 |
| --- | --- | --- |
| test feed consumed | vegetable oil diet | MLCT diet |
| Body weight at a start time of test feed administration (g) | 449 ± 8 | 445 ± 9 |
| body weight at autopsy (g) | 551 ± 16 | 550 ± 20 |
| amount of increased body weight (g) | 102 ± 9 | 106 ± 13 |

TABLE 3

|  | Comparative Example 1 | Comparative Example 2 |
| --- | --- | --- |
| test feed consumed | vegetable oil diet | MCT diet |
| body weight at a start time of test feed administration (g) | 447 ± 6 | 442 ± 3 |
| body weight at autopsy (g) | 538 ± 14 | 520 ± 7 |
| amount of increased body weight (g) | 91 ± 8 | 78 ± 6 |

TABLE 4

|  | Control Example 1 | Example 1 |
| --- | --- | --- |
| test feed consumed | vegetable oil diet | MLCT diet |
| level of epididymal fat (g) | 14.9 ± 0.9 | 12.8 ± 1.1 |
| level of perirenal fat (g) | 17.5 ± 0.6 | 15.5 ± 1.5 |
| level of mesenterium fat (g) | 14.5 ± 1.3 | 11.6 ± 1.0 |
| level of visceral fat (g) | 46.8 ± 2.7 | 39.9 ± 3.2 |

TABLE 5

|  | Comparative Example 1 | Comparative Example 2 |
|---|---|---|
| test feed consumed | vegetable oil diet | MCT diet |
| level of epididymal fat (g) | 12.1 ± 0.5* | 10.8 ± 0.9** |
| level of perirenal fat (g) | 14.0 ± 0.5 | 13.9 ± 1.6 |
| level of mesenterium fat (g) | 10.4 ± 0.5* | 10.1 ± 1.2* |
| level of visceral fat (g) | 36.5 ± 1.0* | 34.8 ± 3.4** |

*statistically significant difference from Control Example 1 present ($p < 0.05$)
**statistically significant difference from Control Example 1 present ($p < 0.01$)

As shown in Tables 2 to 5, the Parkinson's disease model rats that consumed the vegetable oil diet "vegetable oil diet fed group (Comparative Example 1)" and that consumed the MCT diet "MCT diet fed group (Comparative Example 2)" exhibited an increase in body weight that was not significantly different from but lower than the control rats that consumed the vegetable oil diet "control group (Control Example 1)", whereas the level of epididymal fat, the level of mesenterium fat, and the level of visceral fat of these Parkinson's disease model rats were significantly lower. These findings revealed that in the Parkinson's disease model rats that consumed the vegetable oil diet or the MCT diet, a reduction in the amount of visceral fat was caused similarly to Parkinson's disease patients.

The Parkinson's disease model rat that consumed the MLCT diet "MLCT diet fed group (Example 1)" exhibited an increase in body weight at a comparative level to the "control group (Control Example 1)". Also, a significant difference from the "control group (Control Example 1)" with respect to the level of epididymal fat, the level of perirenal fat, the level of mesenterium fat, and the level of visceral fat was not found.

The foregoing results demonstrate that a reduction in the amount of visceral fat was inhibited in the Parkinson's disease model rats that consumed the MLCT diet.

Test Example 2

(1) Experimental Animals
Similar animals to Test Example 1 were used.
(2) Test Feeding
Similarly to Test Example 1, the test feed was designed to give a formulation such that 39% of the total amount of energy was derived from lipids. In this test, according to the formulation shown in Table 6, each of the powered components other than a lipid (rapeseed oil, MCT and LCT) were mixed first, followed by finally mixing the lipid and homogenizing the mixture to prepare a vegetable oil diet and a MCT+LCT diet, respectively.

TABLE 6

| component (% by mass) | vegetable oil diet | MCT + LCT diet |
|---|---|---|
| corn starch | 26.7486 | 26.7486 |
| milk casein | 20 | 20 |
| pregelatinized corn starch | 13.2 | 13.2 |
| granulated sugar | 10 | 10 |
| rapeseed oil (*1) | 20 | 0 |
| MCT + LCT (*2) | 0 | 20 |
| cellulose powder | 5 | 5 |
| mineral mix | 3.5 | 3.5 |
| vitamin mix | 1 | 1 |
| L-cystine | 0.3 | 0.3 |
| choline bitartrate | 0.25 | 0.25 |
| tert-butylhydroquinone | 0.0014 | 0.0014 |

(*1) rapeseed oil: Nisshin OilliO Group, Ltd., trade name "Nisshin Canola"
(*2) MCT + LCT: mixed oil prepared by mixing MCT (medium-chain triglyceride, Nisshin OilliO Group, Ltd., trade name "ODO") with LCT (rapeseed oil, Nisshin OilliO Group, Ltd., trade name "Nisshin Canola") at a ratio of 14:86

(3) Rearing Method
The test was performed with 2 groups in total including one group (five animals) of Parkinson's disease model rats that consumed the MCT+LCT diet "MCT+LCT diet fed group (Comparative Example 3)", and one group (four animals) of control rats that consumed the vegetable oil diet "control group (Control Example 2)". The grouping was carried out such that the average body weight of the rats in each group before starting the test was similar. Rearing was carried out in a similar manner to Test Example 1.
(4) Measurement of Amount of Increased Body Weight
The amount of increased body weight was determined similarly to Test Example 1.
(5) Measurement of Level of Visceral Fat
The level of visceral fat was determined similarly to Test Example 1.
(6) Statistical Processing
In the statistical processing, mean and standard deviation were calculated on measurements of each group, and a Student t-test was employed for a significance test. In the test, a significant difference was determined to be present with a significance level of less than 5%.

TABLE 7

|  | Control Example 2 | Comparative Example 3 |
|---|---|---|
| test feed consumed | vegetable oil diet | MCT + LCT diet |
| at a start time of test feed administration (g) | 393 ± 3 | 391 ± 9 |
| at autopsy (g) | 502 ± 3 | 485 ± 8 |
| amount of increased body weight (g) | 109 ± 4 | 94 ± 5 |

TABLE 8

|  | Control Example 2 | Comparative Example 3 |
|---|---|---|
| test feed consumed | vegetable oil diet | MCT + LCT diet |
| level of epididymal fat (g) | 13.6 ± 0.7 | 10.2 ± 0.6** |
| level of perirenal fat (g) | 13.3 ± 1.0 | 11.2 ± 1.2 |
| level of mesenterium fat (g) | 10.8 ± 0.7 | 9.2 ± 0.4 |
| level of visceral fat (g) | 37.8 ± 2.8 | 30.6 ± 1.9* |

*statistically significant difference from Control Example 2 present ($p < 0.05$)
**statistically significant difference from Control Example 2 present ($p < 0.01$)

As shown in Tables 6 to 8, the Parkinson's disease model rats that consumed the MCT+LCT diet "MCT+LCT diet fed group (Comparative Example 3)" exhibited an increase in body weight that was not significantly different from but lower than the control rats that consumed the vegetable oil diet "control group (Control Example 2)", whereas the level of epididymal fat and the level of visceral fat of these Parkinson's disease model rats were significantly lower. It should be noted that there was no difference in the amount of feed consumed between the two groups.

These findings revealed that in the Parkinson's disease model rats that consumed the MCT+LCT diet, a reduction in the amount of visceral fat was caused similarly to Parkinson's disease patients.

The foregoing results demonstrate that the lipid prepared by merely mixing MCT and LCT did not have the effect of inhibiting visceral fat loss in Parkinson's disease model rats.

The MLCT of the present invention is believed to have an effect of inhibiting a reduction in the amount of visceral fat on Parkinson's disease patient, and in turn prevention or amelioration of body weight loss is expected.

INDUSTRIAL APPLICABILITY

The inhibitor of visceral fat loss of the present invention is useful for the inhibition of peculiar body weight loss found in Parkinson's disease patients.

The invention claimed is:

1. A method for inhibiting visceral fat loss in a subject having Parkinson's disease, the method comprising administering to a subject having Parkinson's disease an effective amount of a lipid obtained by subjecting a medium-chain triglyceride that includes as a constitutive fatty acid at least one of a saturated fatty acid having 8 carbon atoms and a saturated fatty acid having 10 carbon atoms to a transesterification reaction with a vegetable oil, to thereby inhibit visceral fat loss in said patient.

2. The method for inhibiting visceral fat loss according to claim 1, wherein the lipid is obtained by subjecting the medium-chain triglyceride to a transesterification reaction with the vegetable oil at a ratio of 10:90 to 20:80.

* * * * *